US010603009B2

(12) United States Patent
Miyazawa et al.

(10) Patent No.: US 10,603,009 B2
(45) Date of Patent: Mar. 31, 2020

(54) PIEZOELECTRIC DEVICE, PROBE, ELECTRONIC APPARATUS, AND ULTRASONIC IMAGING APPARATUS

(71) Applicant: SEIKO EPSON CORPORATION, Tokyo (JP)

(72) Inventors: Hiromu Miyazawa, Azumino (JP); Masayoshi Yamada, Chino (JP); Hiroshi Ito, Suwa (JP); Tomoaki Nakamura, Chino (JP); Hiroshi Matsuda, Chino (JP); Jiro Tsuruno, Okaya (JP)

(73) Assignee: SEIKO EPSON CORPORATION, Tokyo (JP)

( * ) Notice: Subject to any disclaimer, the term of this patent is extended or adjusted under 35 U.S.C. 154(b) by 732 days.

(21) Appl. No.: 15/167,920

(22) Filed: May 27, 2016

(65) Prior Publication Data
US 2016/0345932 A1 Dec. 1, 2016

(30) Foreign Application Priority Data

May 28, 2015 (JP) ................................. 2015-108929

(51) Int. Cl.
B06B 1/06 (2006.01)
A61B 8/00 (2006.01)
H01L 41/047 (2006.01)

(52) U.S. Cl.
CPC .......... A61B 8/4281 (2013.01); A61B 8/4209 (2013.01); A61B 8/4444 (2013.01);
(Continued)

(58) Field of Classification Search
CPC ........................ A61B 8/4281; H01L 41/0475
See application file for complete search history.

(56) References Cited

U.S. PATENT DOCUMENTS 5,823,962 A * 10/1998 Schaetzle .............. B06B 1/0607
310/366
8,299,550 B2 * 10/2012 Zaitsu .................... B06B 1/0292
257/416
(Continued)

FOREIGN PATENT DOCUMENTS

CN 101192644 A 6/2008
JP 2002-271897 A 9/2002
(Continued)

OTHER PUBLICATIONS

Extended European Search Report dated Oct. 18, 2016 as received in Application No. 16171288.0.

Primary Examiner — Thomas M Dougherty
Assistant Examiner — Karen B Addison
(74) Attorney, Agent, or Firm — Maschoff Brennan

(57) ABSTRACT

A piezoelectric device includes a piezoelectric film having a first surface in contact with a vibrating film and a second surface on the opposite side to the first surface, first and second electrodes that are provided on the second surface of the piezoelectric film and that are disposed at positions away from each other and are short-circuited to each other at a position away from the piezoelectric film, and a third electrode that is provided between the first and second electrodes on the second surface of the piezoelectric film and is disposed at a position away from the first and second electrodes. At least parts of the contours of end portions of the first and second electrodes are defined in parallel to side portions of the third electrode.

11 Claims, 16 Drawing Sheets

(52) U.S. Cl.
CPC ............ *A61B 8/4483* (2013.01); *A61B 8/461* (2013.01); *B06B 1/06* (2013.01); *B06B 1/0622* (2013.01); *B06B 1/0696* (2013.01); *H01L 41/0475* (2013.01); *A61B 8/4477* (2013.01); *B06B 1/0607* (2013.01)

(56) References Cited

U.S. PATENT DOCUMENTS

| | | |
|---|---|---|
| 2002/0105250 A1 | 8/2002 | Klee et al. |
| 2003/0137224 A1 | 7/2003 | Zloter et al. |
| 2009/0001853 A1* | 1/2009 | Adachi ................ A61B 8/4483 310/323.19 |
| 2015/0273526 A1 | 10/2015 | Tsuruno et al. |

FOREIGN PATENT DOCUMENTS

| | | |
|---|---|---|
| JP | 2005-039720 A | 2/2005 |
| JP | 2013-098724 A | 5/2013 |
| JP | 2015-195351 A | 11/2015 |

\* cited by examiner

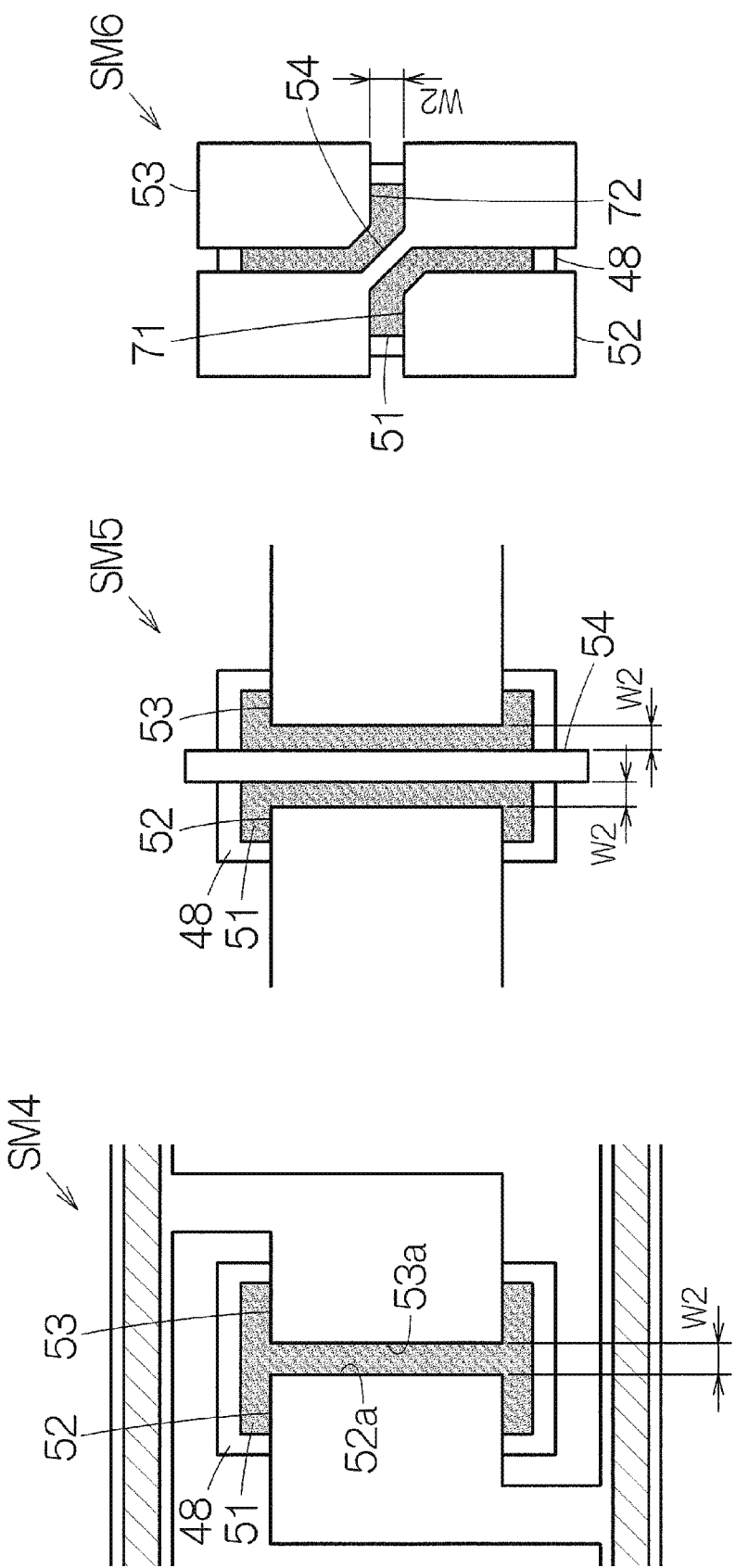

PIEZOELECTRIC DEVICE, PROBE, ELECTRONIC APPARATUS, AND ULTRASONIC IMAGING APPARATUS

CROSS-REFERENCE TO RELATED APPLICATION

The entire disclosure of Japanese Patent Application No. 2015-108929, filed May 28, 2015 is hereby expressly incorporated by reference herein.

BACKGROUND

1. Technical Field

The present invention relates to a piezoelectric device, a probe including the same, and an electronic apparatus and an ultrasonic imaging apparatus using the same.

2. Related Art

JP-A-2002-271897 discloses an array of ultrasonic transducers. Each ultrasonic transducer has two electrodes on a piezoelectric body. A voltage is generated according to the strain $\varepsilon$ of the piezoelectric body. The strain $\varepsilon$ of the piezoelectric body is caused in response to the deformation of a vibrating film. As the distance between the electrodes is increased, a voltage to be generated is increased. Another electrode can be disposed between the two electrodes.

In image generation, a receiving circuit is connected to the array of ultrasonic transducers. The receiving circuit has a stray capacitance. Due to the influence of the stray capacitance, a signal voltage to be measured is decreased.

SUMMARY

An advantage of some aspects of the invention is to provide a piezoelectric device that contributes to an increase in a measured signal voltage by reducing the influence of stray capacitance.

A first aspect of the invention relates to a piezoelectric device including a vibrating film, a piezoelectric film that is provided on the vibrating film and which has a first surface in contact with the vibrating film and a second surface on an opposite side to the first surface, first and second electrodes that are provided on the second surface of the piezoelectric film and that are disposed at positions away from each other and are short-circuited to each other at a position away from the piezoelectric film, and a third electrode that is provided between the first and second electrodes on the second surface of the piezoelectric film and which is disposed at a position away from the first and second electrodes. At least parts of contours of end portions of the first and second electrodes are defined in parallel to side portions of the third electrode.

If the vibrating film performs ultrasonic vibration, the piezoelectric film is strained in response to the deformation of the vibrating film. Surface charges are generated according to the strain $\varepsilon$ of the piezoelectric film. An electric potential is detected between the short-circuited first and second electrodes and the third electrode. The electrostatic capacitance is formed between the end portion of the first electrode and the side portion of the third electrode, and the electrostatic capacitance is formed between the end portion of the second electrode and the side portion of the third electrode. The electrostatic capacitance increases with an increase in the area of the opposite surfaces of each of the first, second, and third electrodes. In this manner, since the influence of the stray capacitance of the receiving circuit on the signal voltage generated in the piezoelectric film is reduced, and a signal voltage that is measured is increased.

A second aspect of the invention is that between the first and second electrodes and the third electrode, a positional relationship to form a voltage path of polarization processing along a direction of strain showing a maximum value may be satisfied. In the piezoelectric film, polarization processing is performed in advance in the use of the piezoelectric effect. According to the polarity of polarization, electric charges move in the piezoelectric film. Therefore, if the electric field path of the polarization processing is combined in the direction of the strain showing the maximum value, the voltage value generated in the piezoelectric film can be maximized. In this manner, it is possible to increase the signal voltage efficiently.

According to a third aspect of the invention, the third electrode may be formed in a band shape passing through a center of the vibrating film in a plan view. The center of the vibrating film is located away from the edge of the fixed vibrating film. Therefore, at the center of the vibrating film, the strain indicates a value close to the maximum value. In this manner, the signal voltage detected from the third electrode formed on the center of the vibrating film can be maximized.

According to a fourth aspect of the invention, in the piezoelectric film, strain may occur in an in-plane direction in a region including the center of the vibrating film. As described above, in the vibrating film, the strain indicates a value close to the maximum value. Therefore, the piezoelectric film on the center can be strained to the maximum extent. In this manner, it is possible to maximize the signal voltage.

According to a fifth aspect of the invention, the piezoelectric film may be located on an inner side rather than along an edge of the vibrating film in a plan view. Since the piezoelectric film does not overlap the shape of the fixed vibrating film, the strain of the vibrating film can be maximized.

According to a sixth aspect of the invention, a center of the piezoelectric film may overlap a center of the vibrating film. By matching the position where the strain of the vibrating film is maximized with the position where the strain of the piezoelectric film is maximized, the signal voltage can be maximized.

According to a seventh aspect of the invention, the vibrating film may have a rectangular shape in a plan view, and the first and second electrodes may be separated from the third electrode in a direction along short sides of the vibrating film. In a rectangle, the sides are perpendicular to each other. Accordingly, since patterning becomes easy, it is possible to increase the arrangement density. If electrodes are separated from each other in a direction along the short sides (any side in a square), the strain of the piezoelectric film occurring in the direction of the short sides is maximized. Therefore, the signal voltage can be maximized.

According to an eighth aspect of the invention, the piezoelectric device may be formed symmetrically with respect to a reference line parallel to long sides of the vibrating film. Since the strain of the piezoelectric film occurring in the short side direction in the reference line is maximized, the signal voltage can be maximized.

According to a ninth aspect of the invention, the third electrode may have a first width in parallel to short sides of the piezoelectric film, and the first and second electrodes may be separated from the third electrode in parallel to the short sides of the piezoelectric film with a second width which is equal to or greater than the first width. Using this configuration, it is possible to increase the receiving sensitivity by reducing the electrostatic capacitance formed between the first and third electrodes and the electrostatic capacitance formed between the second and third electrodes.

According to a tenth aspect of the invention, between the first and third electrodes and between the second and third electrodes, a groove may be formed on the second surface. Since the strain of the piezoelectric film due to sound pressure is concentrated on the groove as the depth of the groove increases, it is possible to increase the receiving sensitivity.

According to an eleventh aspect of the invention, between the first and second electrodes and the third electrode in a plan view, a material other than a conductor may be disposed on the vibrating film. If a conductor is disposed here, a voltage path is diverted toward the conductor. Accordingly, it is not possible to increase the signal voltage that is measured. For example, if a material other than a conductor, such as an insulator, is disposed, it is possible to reliably increase the signal voltage.

According to a twelfth aspect of the invention, as a process of initializing the piezoelectric film, an electric field vector toward the third electrode from the first electrode may be applied, and an electric field vector toward the third electrode from the second electrode may be applied.

According to a thirteenth aspect of the invention, the piezoelectric device may be built into a probe. In this case, the probe may include a plurality of piezoelectric devices.

According to a fourteenth aspect of the invention, the probe may further include a conductor that forms the third electrode in common with the piezoelectric devices arranged in a slice direction. In this case, in the probe, complication of wiring lines can be avoided as much as possible.

According to a fifteenth aspect of the invention, the probe may further include a conductor that forms the first electrode in common with the piezoelectric devices arranged in a scanning direction and a conductor that forms the second electrode in common with the piezoelectric devices arranged in the scanning direction. In this case, complication of wiring lines can be avoided as much as possible.

According to a sixteenth aspect of the invention, the piezoelectric device may be used by being built into an ultrasonic imaging apparatus. In this case, the ultrasonic imaging apparatus may include a plurality of piezoelectric devices.

According to a seventeenth aspect of the invention, the ultrasonic imaging apparatus may further include a conductor that forms the third electrode in common with the piezoelectric devices arranged in a slice direction. In this case, in the ultrasonic imaging apparatus, complication of wiring lines can be avoided as much as possible.

According to an eighteenth aspect of the invention, the ultrasonic imaging apparatus may further include a conductor that forms the first electrode in common with the piezoelectric devices arranged in a scanning direction and a conductor that forms the second electrode in common with the piezoelectric devices arranged in the scanning direction. In this case, in the ultrasonic imaging apparatus, complication of wiring lines can be avoided as much as possible.

According to a nineteenth aspect of the invention, the piezoelectric device may be built into an electronic apparatus. In this case, the electronic apparatus may include a plurality of piezoelectric devices.

BRIEF DESCRIPTION OF THE DRAWINGS

The invention will be described with reference to the accompanying drawings, wherein like numbers reference like elements.

FIGS. 12A to 12C are plan views schematically showing simulation models;

DESCRIPTION OF EXEMPLARY EMBODIMENTS

Hereinafter, an embodiment of the invention will be described with reference to the accompanying diagrams. In addition, the present embodiment to be described below does not unduly limit the content of the invention as defined in the appended claims, and all elements described in the present embodiment are not necessarily indispensable as solving means of the invention.

1. Overall Configuration of an Ultrasonic Diagnostic Apparatus

Figure 1:
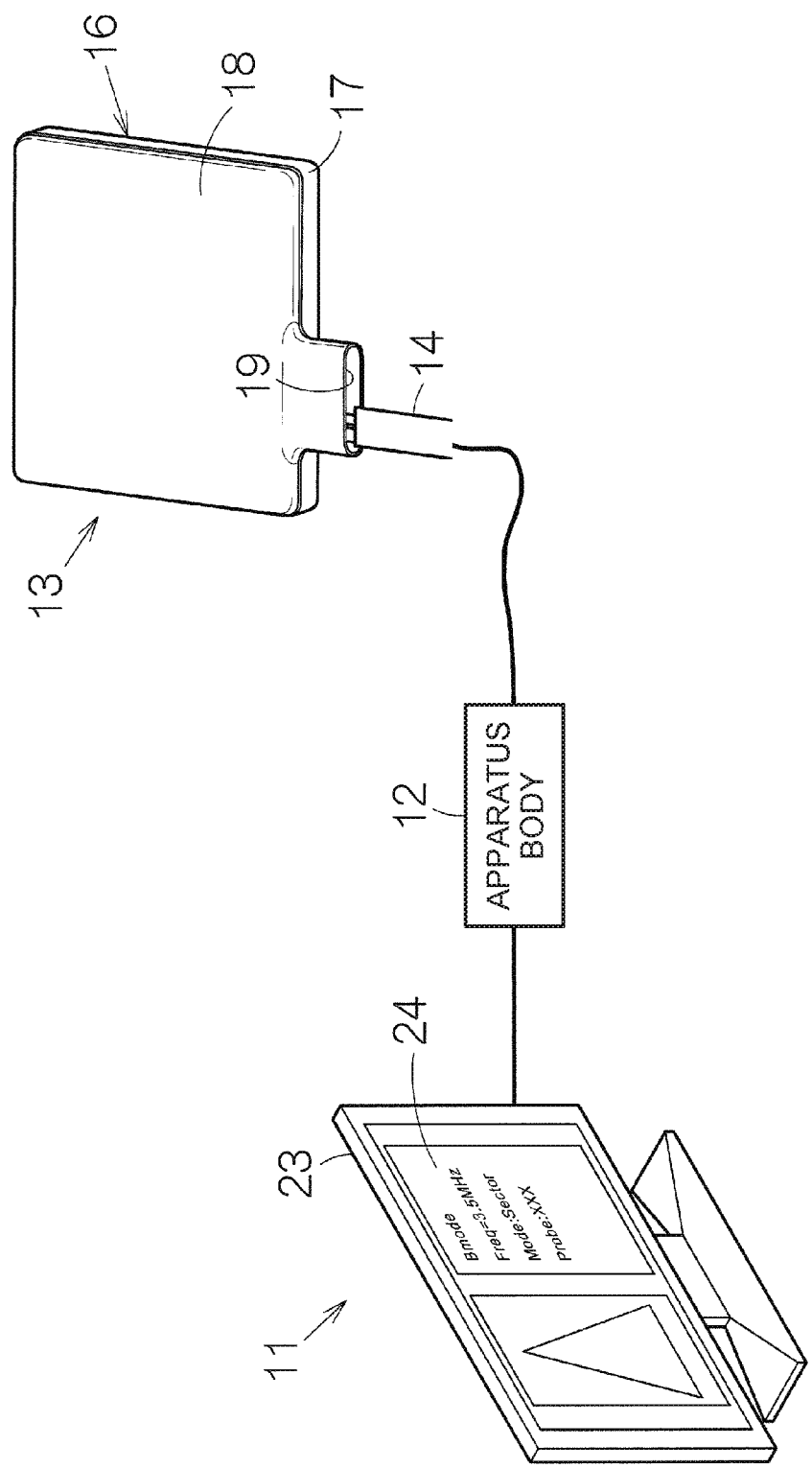
FIG. 1 is a schematic diagram that schematically shows the configuration of an ultrasonic diagnostic apparatus.

FIG. 1 schematically shows the configuration of a specific example of an electronic apparatus according to an embodiment of the invention, that is, the configuration of an ultrasonic diagnostic apparatus (ultrasonic imaging apparatus) 11. The ultrasonic diagnostic apparatus 11 includes an apparatus body 12 and an ultrasonic probe (probe) 13. The apparatus body 12 and the ultrasonic probe 13 are connected to each other by a cable 14. The apparatus body 12 and the ultrasonic probe 13 perform transmission and reception of electrical signals therebetween through the cable 14. A transmission circuit and a receiving circuit are provided in the apparatus body 12. The transmission circuit transmits a driving signal toward the ultrasonic probe 13. The receiving circuit receives a detection signal from the ultrasonic probe 13.

The ultrasonic probe 13 includes a housing 16. The housing 16 includes a front side body 17 and a back side body 18. The front side body 17 and the back side body 18 are coupled to each other. Between the front side body 17 and the back side body 18, a cable port 19 is provided between the coupling surface of the front side body 17 and the coupling surface of the back side body 18. The cable 14 is disposed in the cable port 19. As will be described later, an ultrasonic device unit is supported by the housing 16. The ultrasonic device unit transmits an ultrasonic wave in response to the reception of a driving signal, receives a reflected wave, and outputs a detection signal.

A display device 23 is connected to the apparatus body 12. A display panel 24 is built into the display device 23. As will be described later, an image based on the ultrasonic wave detected by the ultrasonic probe 13 is displayed on the screen of the display panel 24. An imaged detection result is displayed on the screen of the display panel 24.

Figure 2:
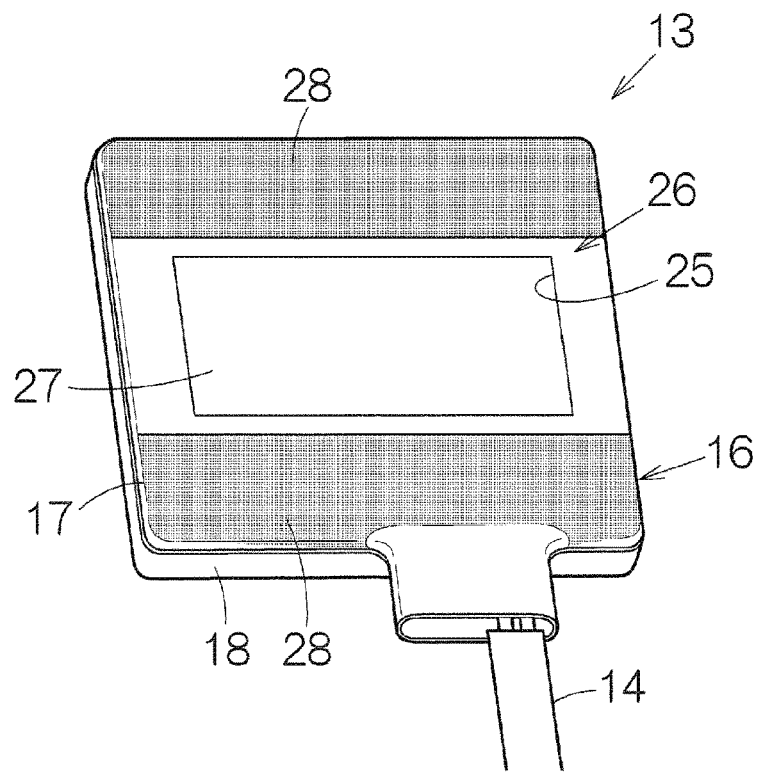
FIG. 2 is a perspective view schematically showing the surface of an ultrasonic probe.

As shown in FIG. 2, an opening 25 is formed in the front side body 17 of the housing 16. The opening 25 faces the housing space provided in the housing 16. An ultrasonic device unit 26 is disposed in the housing space. The ultrasonic device unit 26 includes an acoustic matching layer 27. The acoustic matching layer 27 is formed of, for example, silicone resin. The acoustic matching layer 27 has acoustic impedance (for example, 1.0 [MRayl] to 1.5 [MRayl]) close to the acoustic impedance 1.5 [MRayl] of the living body. The ultrasonic device unit 26 outputs an ultrasonic wave from the surface and receives a reflected wave of the ultrasonic wave. The ultrasonic diagnostic apparatus 11 or the ultrasonic probe 13 may have other structures.

The ultrasonic probe 13 has an adhesive layer 28. The adhesive layer 28 is, for example, laminated on the surface of the front side body 17. The adhesive layer 28 has adhesion to an object, such as the skin. The ultrasonic probe 13 can be attached to the object due to the adhesive layer 28. If the ultrasonic probe 13 is attached in this manner, the acoustic matching layer 27 is in close contact with the object.

2. Configuration of the Ultrasonic Device Unit

Figure 3:
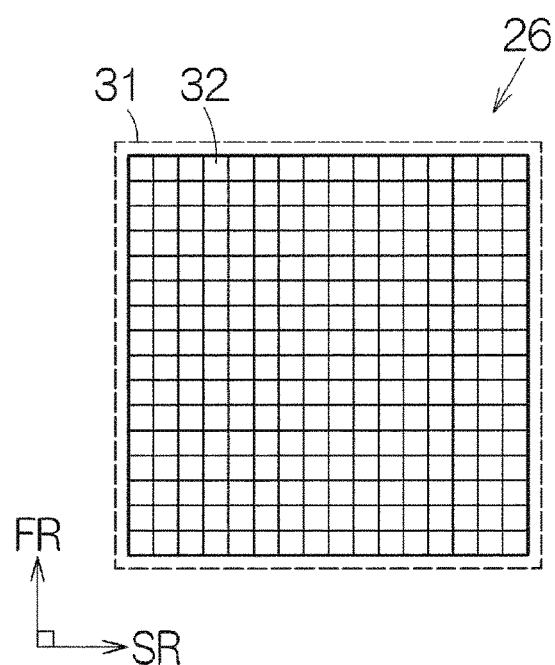
FIG. 3 is an enlarged partial plan view schematically showing the configuration of an ultrasonic device unit according to one embodiment of the invention.

FIG. 3 conceptually shows the configuration of the ultrasonic device unit 26 according to the embodiment. The ultrasonic device unit 26 includes an element array (piezoelectric device group) 31. The element array 31 includes ultrasonic transducers 32 that are disposed in an array. In FIG. 3, the ultrasonic transducer 32 is expressed per square mass. Here, the ultrasonic transducers 32 of N rows and L columns are arranged in the element array 31. That is, ultrasonic transducer columns of N rows are arranged in a first direction (hereinafter, referred to as a "slice direction") FR, and ultrasonic transducer columns of L columns are arranged in a second direction (hereinafter, referred to as a "scanning direction") SR perpendicular to the slice direction. As will be described later, one ultrasonic transducer 32 includes a transmission unit and a receiving unit. The transmission unit transmits an ultrasonic wave having a frequency determined according to the supply of an electrical signal. The receiving unit receives the ultrasonic wave having a determined frequency, and converts the ultrasonic wave into an electrical signal.

Figure 4:
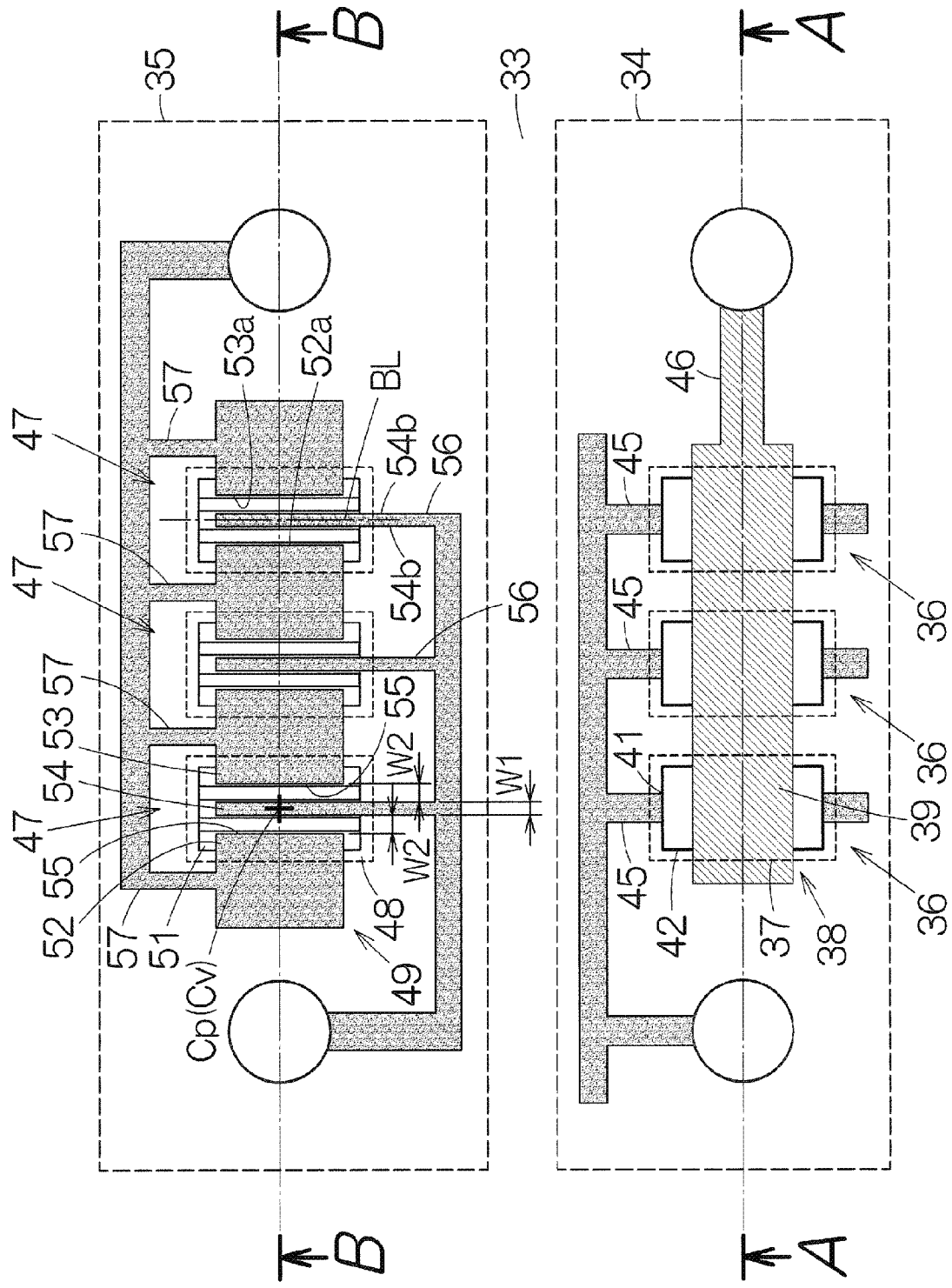
FIG. 4 is an enlarged partial plan view showing the structure of an ultrasonic device in detail.

FIG. 4 shows the structure of the ultrasonic device unit 26 according to a first embodiment of the invention in more detail. The ultrasonic device unit 26 includes a base 33. A transmission unit 34 and a receiving unit 35 are formed on the base 33. The ultrasonic device unit 26 is formed as one ultrasonic transducer element chip. The transmission unit 34 includes a plurality of first piezoelectric devices 36. Each of the first piezoelectric devices 36 includes a vibrating film 37. The details of the vibrating film 37 will be described later. In FIG. 4, the shape of the vibrating film 37 is drawn with a dotted line in a plan view from a direction perpendicular to the surface of the vibrating film 37 (in plan view from the thickness direction of the substrate). A piezoelectric element 38 is formed on the vibrating film 37. In the piezoelectric element 38, a piezoelectric film 42 is interposed between an upper electrode 39 and a lower electrode 41, as will be described later. These are superimposed in order.

A plurality of first signal electrode lines 45 are formed on the surface of the base 33. The first signal electrode lines 45 extend in the column direction (slice direction) of the array in parallel to each other. One first signal electrode line 45 is provided for each ultrasonic transducer element 32. The first signal electrode line 45 forms the lower electrode 41 in each of the first piezoelectric devices 36. For the first signal electrode line 45, for example, a laminated film of titanium (Ti), iridium (Ir), platinum (Pt), and titanium (Ti) can be used. However, other conductive materials may be used for the first signal electrode line 45.

First common electrode lines 46 extending in the row direction (scanning direction) of the array are formed on the surface of the base 33. The first common electrode lines 46 extend in the row direction of the array in parallel to each other. In all of the ultrasonic transducer 32, the first common electrode lines 46 can be combined into one. The first common electrode line 46 forms the upper electrode 39 in each of the first piezoelectric devices 36. The first common electrode line 46 can be formed of, for example, iridium (Ir). However, other conductive materials may be used for the first common electrode line 46.

The supply of power to the first piezoelectric device 36 is switched for each ultrasonic transducer 32. Since the first piezoelectric devices 36 in each ultrasonic transducer 32 output ultrasonic waves at the same time, the number of first piezoelectric devices 36 in each ultrasonic transducer 32 can be determined according to the output level of the ultrasonic wave.

The receiving unit 35 includes a plurality of second piezoelectric devices 47. Each of the second piezoelectric devices 47 includes a vibrating film 48. The details of the vibrating film 48 will be described later. In FIG. 4, the shape of the vibrating film 48 is drawn with a dotted line in a plan view from a direction perpendicular to the surface of the vibrating film 48 (in plan view from the thickness direction of the substrate). On the vibrating film 48, a piezoelectric element 49 according to the present embodiment is formed. In the piezoelectric element 49, a first electrode 52, a second electrode 53, and a third electrode 54 are formed on a piezoelectric film 51, as will be described more fully below. As shown in FIG. 4, the shape of end portions 52a and 53a of the first and second electrodes 52 and 53 are defined in parallel to side portions 54b and 54b of the third electrode 54. The end portions 52a and 53a and the side portions 54b and 54b may face each other, for example.

Here, the vibrating film 48 has a rectangular shape in a plan view (when viewed from a direction perpendicular to the surface of the vibrating film 48). The piezoelectric film 51 has a rectangular shape located on the inner side of the shape of the vibrating film 48 in a plan view. The center Cp of the piezoelectric film 51 overlaps the center Cv of the vibrating film 48. Accordingly, in the piezoelectric film 51, strain occurs in an in-plane direction in a region including the center Cv of the vibrating film 48. As an alternative to the rectangle, a square may be applied. In addition, the shapes of the vibrating film 48 and the piezoelectric film 51 may not only be the rectangles but also polygons or ellipses.

The third electrode 54 is formed in a band shape passing through the center Cv of the vibrating film 48 in plan view. The first and second electrodes 52 and 53 are separated from the third electrode 54 in a direction along the short sides of the vibrating film 48. The third electrode 54 has a first width W1 in parallel to the short side of the piezoelectric film 51, and the first and second electrodes 52 and 53 are separated from the third electrode 54 in parallel to the short side of the piezoelectric film 51 with a second width W2 equal to or greater than the first width W1. The first and second electrodes 52 and 53 are separated from the short sides of the vibrating film 48, and are disposed between the short sides. Between the first and third electrodes 52 and 54 and between the second and third electrodes 53 and 54, a groove 55 is formed on the surface (second page) of the piezoelectric film 51. Each second piezoelectric device 47 is formed symmetrically with respect to a reference line BL parallel to the long sides of the vibrating film 48. Also in a case where the vibrating film 48 and the piezoelectric film 51 do not have rectangular shapes, each second piezoelectric device 47 is formed symmetrically with respect to the reference line BL passing through the center Cp.

A plurality of second signal electrode lines 56 are formed on the surface of the base 33. The second signal electrode lines 56 extend in the column direction (slice direction) of the array in parallel to each other. One second signal electrode line 56 is provided for each ultrasonic transducer element 32. The second signal electrode line 56 forms the third electrode 54 in each of the second piezoelectric devices 47. For the second signal electrode line 56, for example, iridium (Ir) can be used. However, other conductive materials may be used for the second signal electrode line 56.

Second common electrode lines (conductors) 57 extending in the column direction of the array in parallel to each other are formed on the surface of the base 33. One second common electrode line 57 is provided for each ultrasonic transducer element 32. The second common electrode line 57 is connected to the first and second electrodes 52 and 53. Accordingly, the first and second electrodes 52 and 53 are short-circuited to each other at a position away from the piezoelectric film 51. The second common electrode line 57 can be formed of, for example, iridium (Ir). However, other conductive materials may be used for the second common electrode line 57.

Figure 5:
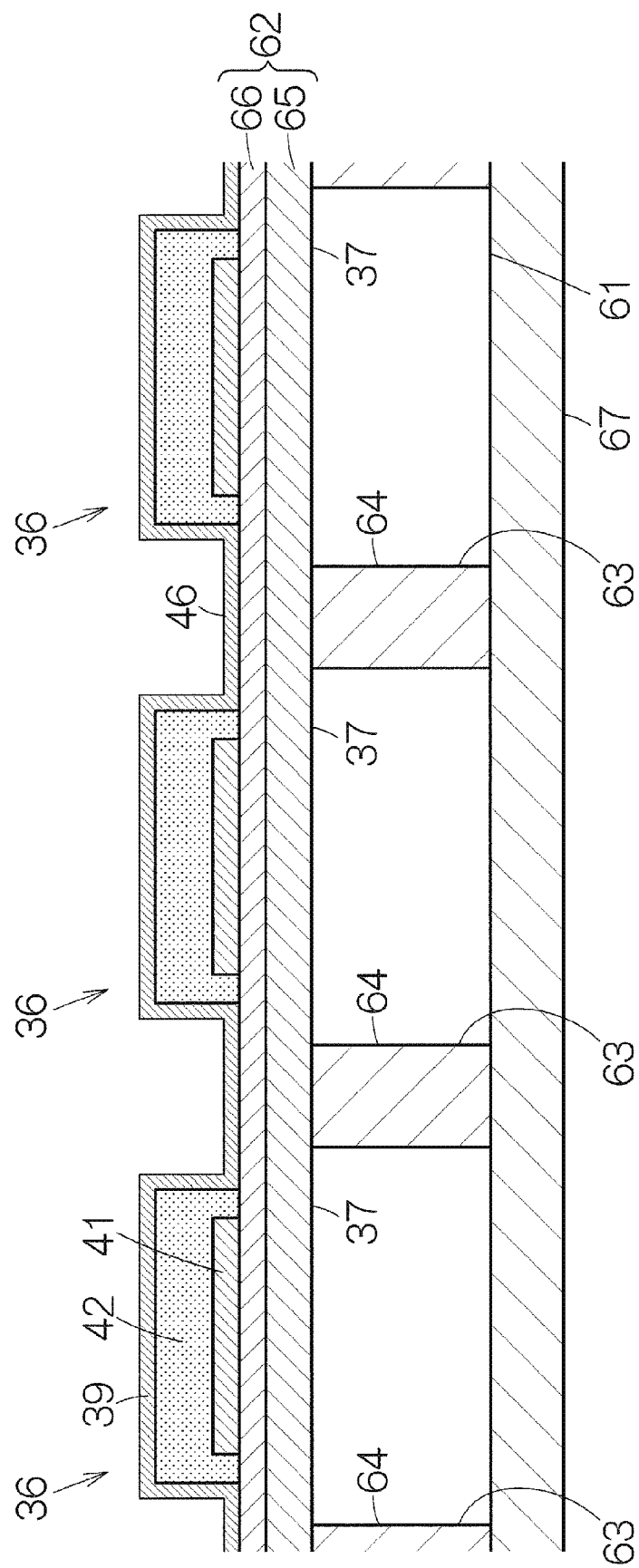
FIG. 5 is a partial sectional view taken along the line A-A of FIG. 4.

FIG. 5 shows the details of the transmission unit 34. As shown in FIG. 5, the base 33 includes a substrate 61 and a flexible film 62. The flexible film 62 is formed on the entire surface of the substrate 61. On the substrate 61, an opening 63 is formed in each first piezoelectric device 36. The openings 63 are disposed in the form of an array for the substrate 61. A partition wall 64 is provided between two adjacent openings 63. The adjacent openings 63 are partitioned by the partition wall 64.

The flexible film 62 is formed by a silicon oxide (SiO$_2$) layer 65 laminated on the surface of the substrate 61 and a zirconium oxide (ZrO$_2$) layer 66 laminated on the surface of the silicon oxide layer 65. The flexible film 62 is in contact with each opening 63. In this manner, a part of the flexible film 62 forms the vibrating film 37 corresponding to the shape of the opening 63.

The first signal electrode line 45, the piezoelectric film 42, and the first common electrode line 46 are laminated in order on the surface of the vibrating film 37. The piezoelectric film 42 can be formed of, for example, lead zirconate titanate (PZT). Other piezoelectric materials may be used for the piezoelectric film 42. Here, the piezoelectric film 42 completely covers the surface of the first signal electrode line 45 under the first common electrode line 46. A short circuit between the first signal electrode line 45 and the first common electrode line 46 can be avoided due to the piezoelectric film 42.

The acoustic matching layer 27 covers the element array 31. The acoustic matching layer 27 is laminated on the surface of the base 33. A reinforcing plate 67 as a backing material is bonded to the back surface of the base 33. The reinforcing plate 67 is formed in a flat plate shape. The back surface of the base 33 overlaps the surface of the reinforcing plate 67. The surface of the reinforcing plate 67 is bonded to the back surface of the base 33. In such bonding, the reinforcing plate 67 may be bonded to the base 33 with an adhesive. The reinforcing plate 67 increases the rigidity of the base 33. The reinforcing plate 67 can include a rigid base, for example. Such a base may be formed of a metal material, such as a 42 alloy (iron-nickel alloy).

Figure 6:
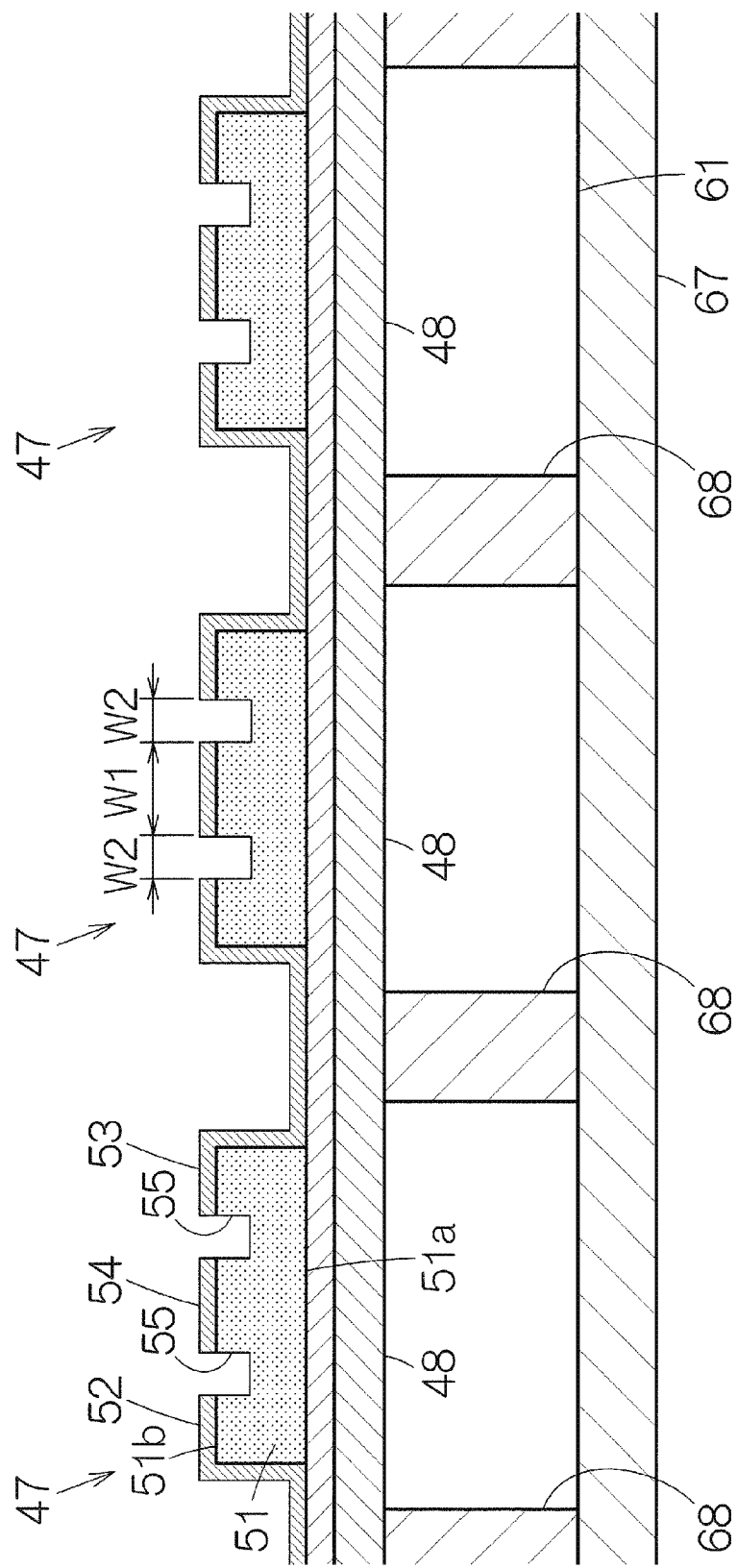
FIG. 6 is a partial sectional view taken along the line B-B of FIG. 4.

FIG. 6 shows the details of the receiving unit 35. As shown in FIG. 6, on the substrate 61, an opening 68 is formed in each second piezoelectric device 47. Corresponding to the shape of the opening 68, a part of the flexible film 62 forms the vibrating film 48. A first surface 51a of the piezoelectric film 51 is in contact with the vibrating film 48. The first electrode 52, the second electrode 53, and the third electrode 54 are laminated on a second surface 51b on the opposite side (back side) to the first surface 51a. The piezoelectric film 51 can be formed of, for example, lead zirconate titanate (PZT). Other piezoelectric materials may be used for the piezoelectric film 42. On the vibrating film 48 between the first electrode 52, the second electrode 53, and the third electrode 54 in a plan view, a material (here, a zirconium oxide layer 66) other than a conductor is disposed.

3. Operation of the Ultrasonic Diagnostic Apparatus

Next, the operation of the ultrasonic diagnostic apparatus 11 will be briefly described. A driving signal is transmitted to the ultrasonic probe 13 from the apparatus body 12. Then, in the transmission unit 34, a pulse signal is supplied to the first piezoelectric device 36. The pulse signal is supplied to the piezoelectric element 38 through the first signal electrode line 45 and the first common electrode line 46. In each first piezoelectric device 36, an electric field is applied to the piezoelectric film 42 between the upper electrode 39 and the lower electrode 41. The piezoelectric film 42 vibrates at a frequency of an ultrasonic wave. The vibration of the piezoelectric film 42 is transmitted to the vibrating film 37. Accordingly, the vibrating film 37 performs ultrasonic vibration. As a result, a desired ultrasonic beam is emitted toward a subject (for example, the inside of a human body).

In the receiving unit 35, an ultrasonic wave is applied to each second piezoelectric device 47. The reflected wave of the ultrasonic wave vibrates the vibrating film 48. Ultrasonic vibration of the vibrating film 48 causes the piezoelectric film 51 to perform ultrasonic vibration at a desired frequency. If the vibrating film 48 performs ultrasonic vibration, the piezoelectric film 51 is strained according to the deformation of the vibrating film 48. Surface charges are generated according to the strain ε of the piezoelectric film 51. An electric potential is detected between the short-circuited first and second electrodes 52 and 53 and the third electrode 54. The electric potential is output as a detection signal from the second signal electrode line 56 and the second common electrode line 57.

The receiving circuit generates an ultrasonic image based on the detection signal. In such generation of an ultrasonic image, transmission and reception of ultrasonic waves are repeated. A linear scan or a sector scan is realized. An image signal is transmitted to the display device 23 from the receiving circuit. Based on the image signal, an ultrasonic image is displayed on the screen of the display panel 24.

In such generation of an ultrasonic image, in the second piezoelectric device 47, an electrostatic capacitance is formed between the end portion 52a of the first electrode 52 and the side portion 54b of the third electrode 54, and an electrostatic capacitance is formed between the end portion 53a of the second electrode 53 and the side portion 54b of the third electrode 54. The electrostatic capacitance increases with an increase in the area of opposite surfaces. Accordingly, since the influence of the stray capacitance of the receiving circuit on the signal voltage detected between the first and third electrodes 52 and 54 and between the second and third electrodes 53 and 54 is reduced, a signal voltage that is measured is increased.

The third electrode 54 is formed in a band shape passing through the center Cv of the vibrating film 48 in a plan view. The center Cv is separated from the edge of the opening 63 that is a boundary for a region where the vibrating film 48 is fixed to the substrate 61. Therefore, at the center Cv, the strain ε indicates a value close to the maximum value. In this manner, the signal voltage detected between the first and third electrodes 52 and 54 and between the second and third electrodes 53 and 54 can be maximized.

In addition, in the piezoelectric film 51, strain occurs in an in-plane direction in a region including the center Cv of the vibrating film 48. As described above, in the vibrating film 48, at the center Cv, the strain ε indicates a value close to the maximum value. Therefore, since the piezoelectric film 51 on the center Cv can be strained to the maximum extent, the signal voltage detected between the first and third electrodes 52 and 54 and between the second and third electrodes 53 and 54 can be maximized. Here, the center Cp of the piezoelectric film 51 overlaps the center Cv of the vibrating film 48. Since the piezoelectric film 51 is also easily strained at the same center Cv as the vibrating film 48, the strain ε of the vibrating film 48 can be maximized.

The piezoelectric film 51 is located on the inside rather than corresponding to the shape of the vibrating film 48 in a plan view. Here, the vibrating film 48 and the piezoelectric film 51 have a rectangular shape in a plan view. In a rectangle, the sides are perpendicular to each other. Accordingly, since patterning becomes easy, it is possible to increase the arrangement density. In this case, the first and second electrodes 52 and 53 are separated from the third electrode 54 in a direction along the short sides of the vibrating film 48. If the electrodes 52 and 53 are separated from the third electrode 54 in the direction along the short sides of the vibrating film 48, the strain of the piezoelectric film 51 occurring in the direction of the short sides is maximized. Therefore, the signal voltage can be maximized. In addition, since the piezoelectric film 51 does not overlap the shape of the vibrating film 48, the strain ε of the vibrating film 48 can be maximized. Here, since the second piezoelectric device 47 is formed symmetrically with respect to the reference line BL in parallel to the long sides of the vibrating film 48, the strain ε of the vibrating film 48 can be maximized in the reference line BL. Here, the third electrode 54 is provided so as to overlap the reference line BL. That is, the second piezoelectric device 47 is formed line-symmetrically with respect to the third electrode 54.

As described above, in the second piezoelectric device 47, a material other than a conductor may be disposed on the vibrating film 48 between the first electrode 52, the second electrode 53, and the third electrode 54 in a plan view. If a conductor is disposed here, a voltage path is diverted toward the conductor. Accordingly, it is not possible to increase the signal voltage that is measured. For example, if a material other than a conductor, such as an insulator, is disposed, it is possible to reliably increase the signal voltage.

4. Optimal Position of an Electrode

Figure 7:
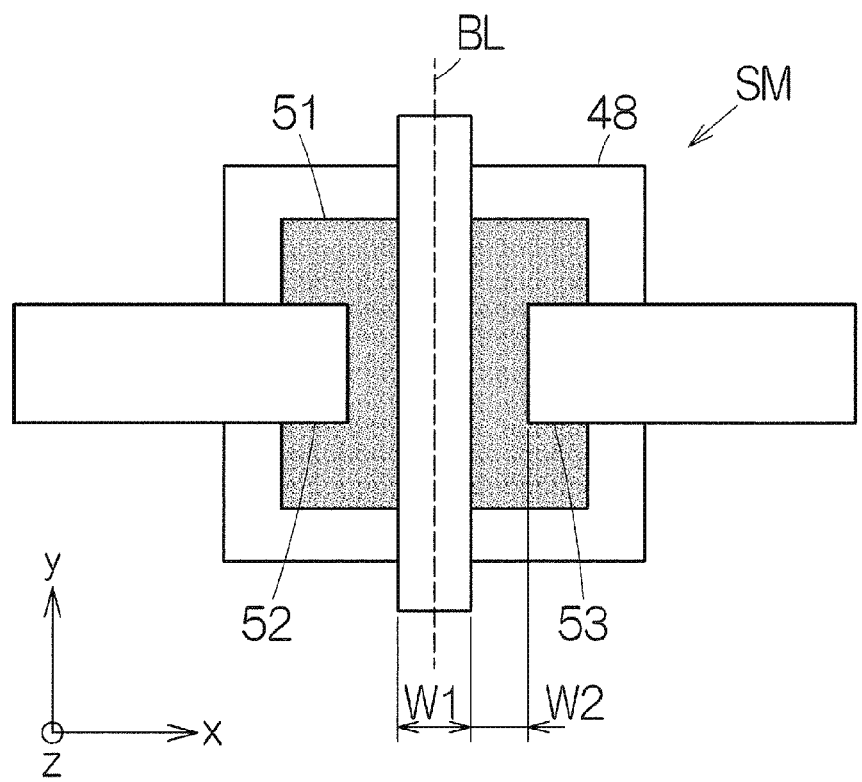
FIG. 7 is a plan view schematically showing a simulation model.

The present inventors calculated the strain of the piezoelectric film 51. As shown in FIG. 7, in such calculation, a simulation model SM of the second piezoelectric device 47 was constructed. The shapes of the vibrating film 48 and the piezoelectric film 51 were set to be squares.

Simulation was performed using a finite element method for realizing the piezoelectric effect. The length of the short side of the shape of the vibrating film 48 was 40 μm, and the length of the short side of the piezoelectric film 51 was 32 μm. In addition, the vibrating film 48 includes $SiO_2$ (1000 nm), $ZrO_2$ (400 nm), and PZT (1350 nm) in order from the bottom. The thickness of each of the first, second, and third electrodes 52, 53, and 54 was 50 nm. As the piezoelectric tensor and the stiffness tensor of PZT used in the simulation, a data set of PZT-5H was adopted. In this case, the principal axis of the tensor was set to a direction perpendicular to the reference line BL (direction in which an initialization electric field was applied). The Young's moduli of $SiO_2$ and $ZrO_2$ were 75 GPa and 190 GPa, respectively. The Young's moduli of the first, second, and third electrodes 52, 53, and 54 were 200 GPa. 1 atmosphere was applied to the vibrating film 48 from above, and the strain at that time was examined.

Figure 8A:
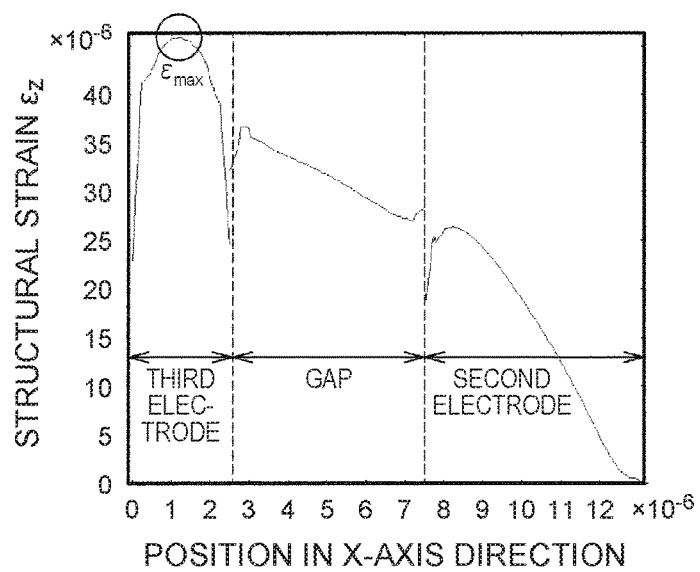
FIGS. 8A to 8C are graphs showing the calculation result of the structural strain of a piezoelectric film.
Figure 8B:
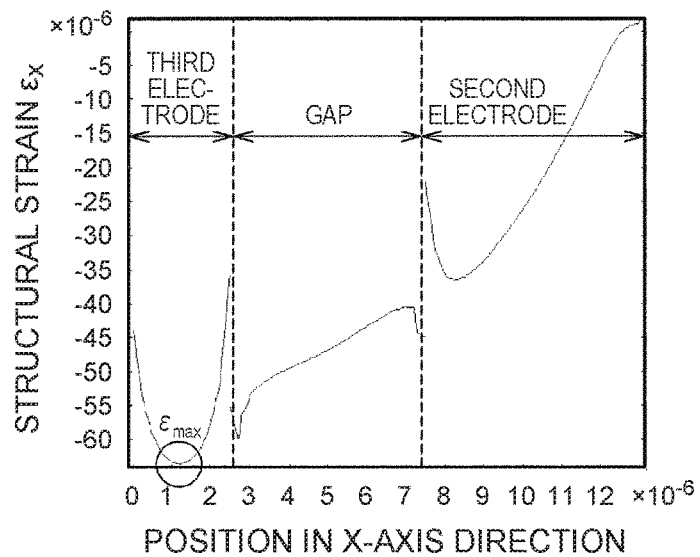
Figure 8C:
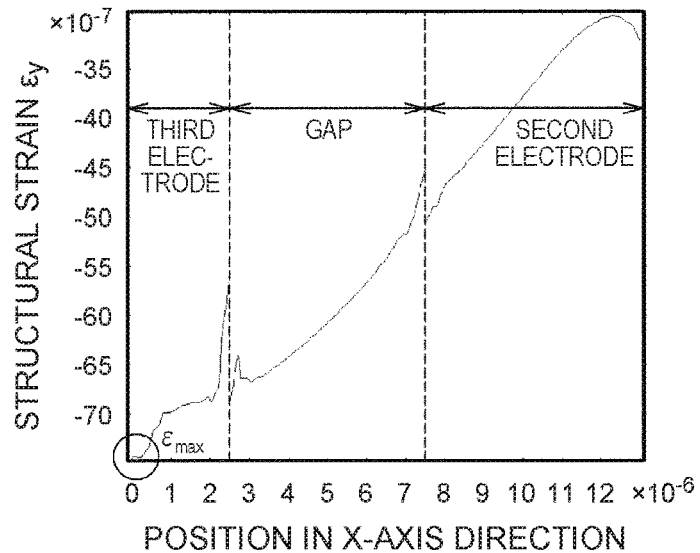

The first width W1 of the third electrode 54 was set to 5 [μm]. The distance (=second width W2) between the first and third electrodes 52 and 54 and the distance (=second width W2) between the second and third electrodes 53 and 54 were set to 5 [μm]. x, y, and z axes were set in the simulation model SM. Since the second piezoelectric device 47 is formed symmetrically with respect to the reference line BL, an x-axis direction strain εx, a y-axis direction strain εy, and a z-axis direction strain εz were calculated for each x-axis direction position on one side of the reference line BL. The x axis is perpendicular to the reference line BL, and the y axis is parallel to the reference line BL. As a result, as shown in FIGS. 8A to 8C, the maximum value of strain was obtained in any direction immediately below the third electrode 54.

This will be described in more detail. The value of the z-axis direction strain εz was the maximum immediately below the third electrode 54, and was $46 \times 10^{-6}$. Similarly, absolute values of the x-axis direction strain εx and the y-axis direction strain εy were the maximum immediately below the third electrode 54, and were $-64 \times 10^{-6}$ and $-75 \times 10^{-7}$, respectively. In particular, it can be seen that the x-axis direction strain εx is about 10 times larger than the y-axis direction strain εy. That is, in the invention, a direction in which the strain is the maximum (x-axis direction) and the reference line BL are perpendicular to each other. When such an electrode arrangement is adopted, the receiving sensitivity is maximized.

In the second piezoelectric device 47, the groove 55 is formed between the first and third electrodes 52 and 54 and between the second and third electrodes 53 and 54. The groove 55 acts advantageously when increasing the receiving sensitivity. This is because the strain of the piezoelectric film 51 due to sound pressure is concentrated on the groove 55 as the depth of the groove 55 increases. If the thickness of the piezoelectric film 51 reduced by the groove 55 is ⅔ or less of the original thickness, an increase in the receiving sensitivity of 20% or more is observed.

Prior to the receiving process, the piezoelectric film 51 may be subjected to polarization processing. In the invention, polarization processing is performed by an electric field vector from the first electrode 52 to the third electrode 54, and at the same time, polarization processing is performed by an electric field vector from the second electrode 53 to the third electrode 54. In this manner, an electric field for the polarization processing of the piezoelectric body is applied in a direction of the strain $\varepsilon$ showing the maximum value (axis of symmetry of the short sides of the vibrating film). When this condition is satisfied, a received signal voltage can be efficiently increased.

5. First Width of the Third Electrode

Figure 9A:
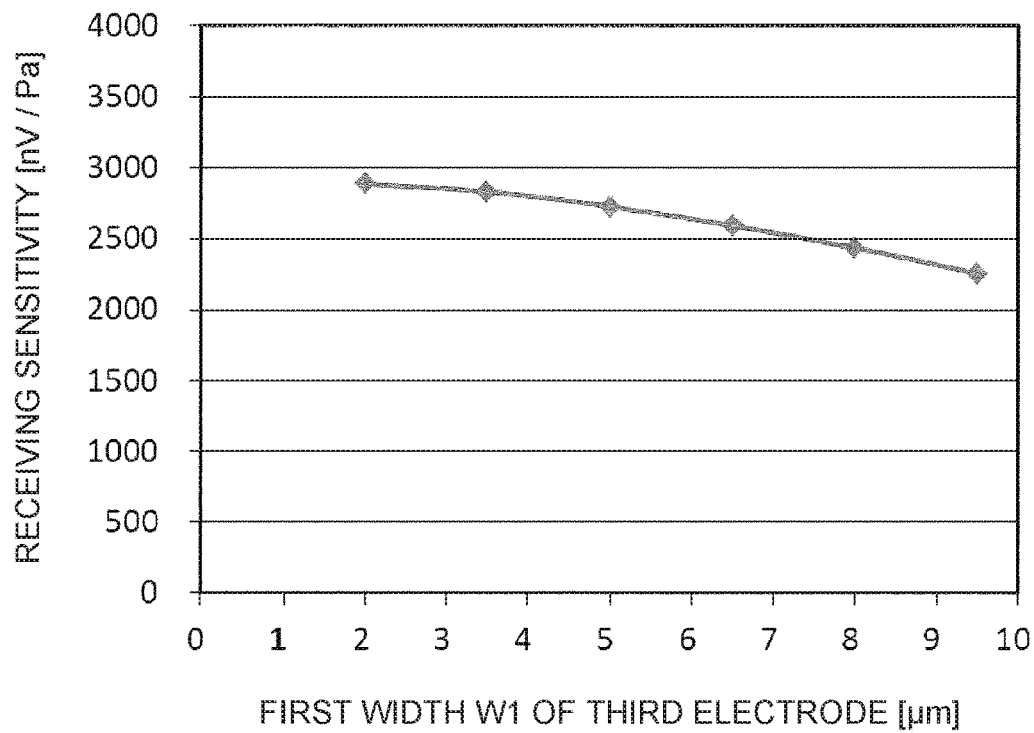
FIG. 9A is a graph showing the relationship between the first width of a third electrode and the receiving sensitivity.
Figure 9B:
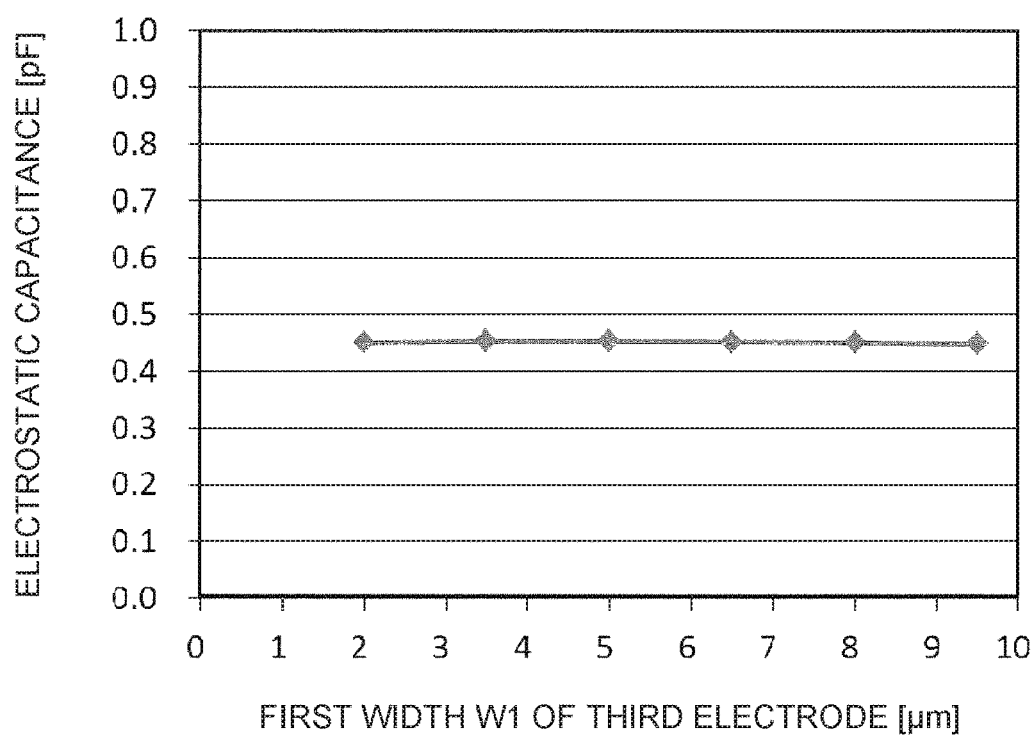
FIG. 9B is a graph showing the relationship between the first width of the third electrode and the electrostatic capacitance.

The present inventors examined the influence of the first width W1 of the third electrode. The receiving sensitivity and the electrostatic capacitance were calculated in the simulation model SM of the second piezoelectric device 47. In such calculation, the first width W1 of the third electrode 54 was changed. The distance (=second width W2) between the first and third electrodes 52 and 54 and the distance (=second width W2) between the second and third electrodes 53 and 54 were fixed to 5 [μm]. As a result, as shown in FIGS. 9A and 9B, it was confirmed that the receiving sensitivity was increased if the first width W1 of the third electrode 54 was reduced. It was confirmed that the electrostatic capacitance was maintained even if the first width W1 was reduced. Assuming that a charge, electrostatic capacitance, and a voltage in a capacitor are Q, C, and V, the relationship of Q=C·V is satisfied. In a case where the electrostatic capacitance is fixed, in order to increase the voltage V, it is necessary to increase the charge Q itself. The charge Q depends on the piezoelectric strain due to sound pressure. Therefore, the reason why the receiving sensitivity is increased is that the binding force generated by the third electrode 54 is reduced if the first width W1 is reduced and as a result, the strain of the piezoelectric film 51 due to sound pressure is increased.

6. Second Width Between Electrodes

Figure 10A:
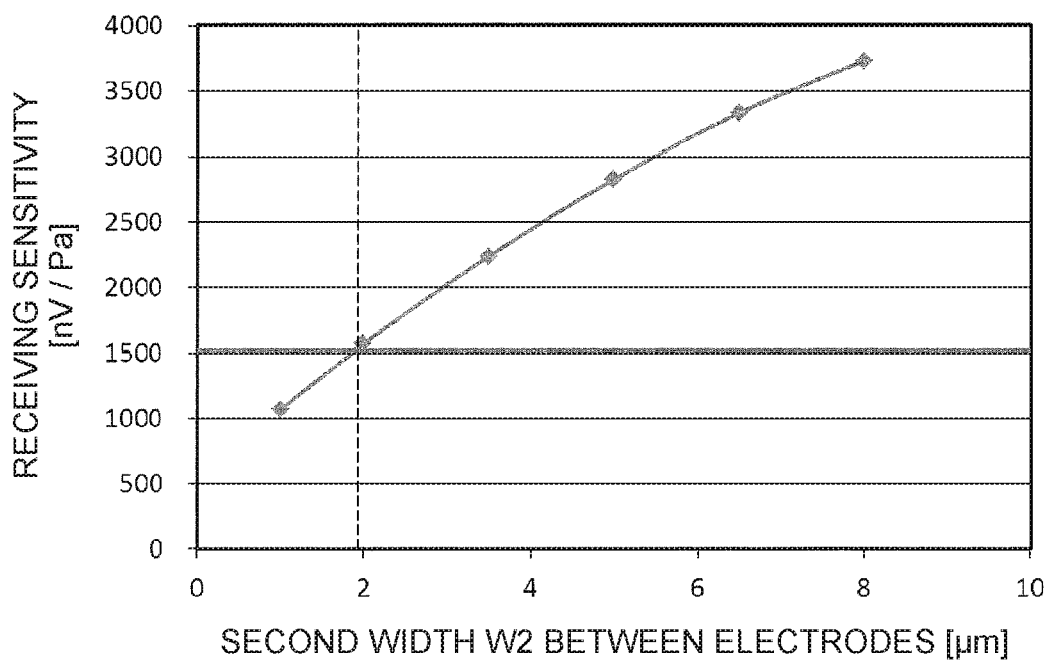
FIG. 10A is a graph showing the relationship between the distance between electrodes (=second width) and the receiving sensitivity.
Figure 10B:
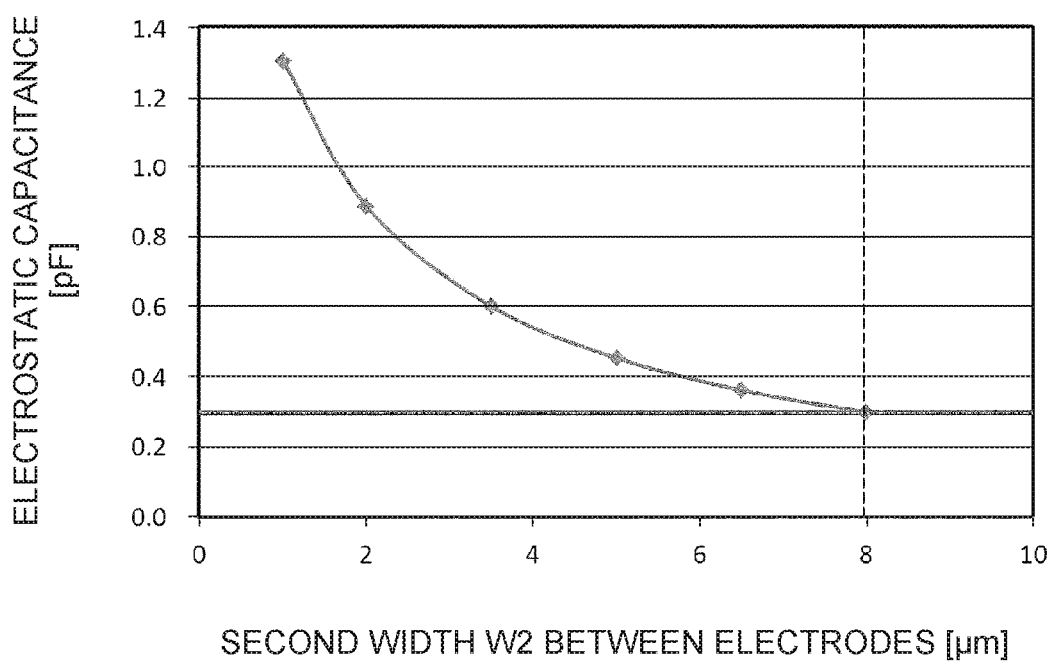
FIG. 10B is a graph showing the relationship between the distance between electrodes (=second width) and the electrostatic capacitance.

The present inventors examined the influence of the distance (=second width W2) between the first and second electrodes 52 and 53 and the third electrode 54. The receiving sensitivity and the electrostatic capacitance were calculated in the simulation model SM of the second piezoelectric device 47. In such calculation, the distance (=second width W2) between the first and third electrodes 52 and 54 and the distance (=second width W2) between the second and third electrodes 53 and 54 were changed. The first width W1 of the third electrode 54 was fixed to 5 [μm]. As a result, as shown in FIGS. 10A and 10B, it was confirmed that the receiving sensitivity was increased if the distance (=second width W2) between the first and third electrodes 52 and 54 and the distance (=second width W2) between the second and third electrodes 53 and 54 was increased. This is because the electrostatic capacitance C is reduced and the receiving voltage V is increased if the second width W2 is increased. The relationship of Q=C·V is satisfied. Accordingly, if a distance d between electrodes is increased to reduce the electrostatic capacitance C, the voltage V is increased in a case where the charge Q is fixed. In this manner, the first and second electrodes 52 and 53 are separated from the third electrode 54 in parallel to the short side of the piezoelectric film 51 with the second width W2 equal to or greater than the first width W1. Therefore, since the electrostatic capacitance C is reduced, it is possible to increase the receiving sensitivity.

7. Advantages of the Second Piezoelectric Device

Figure 11A:
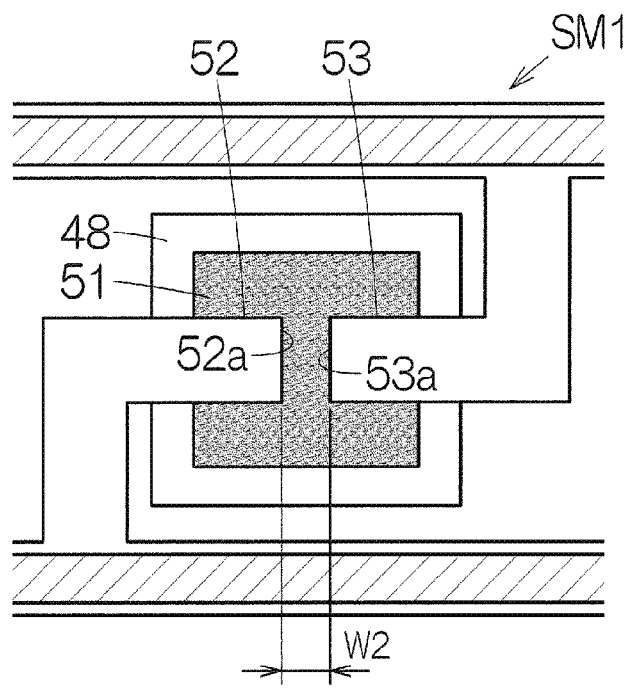
FIGS. 11A to 11C are plan views schematically showing simulation models.
Figure 11B:
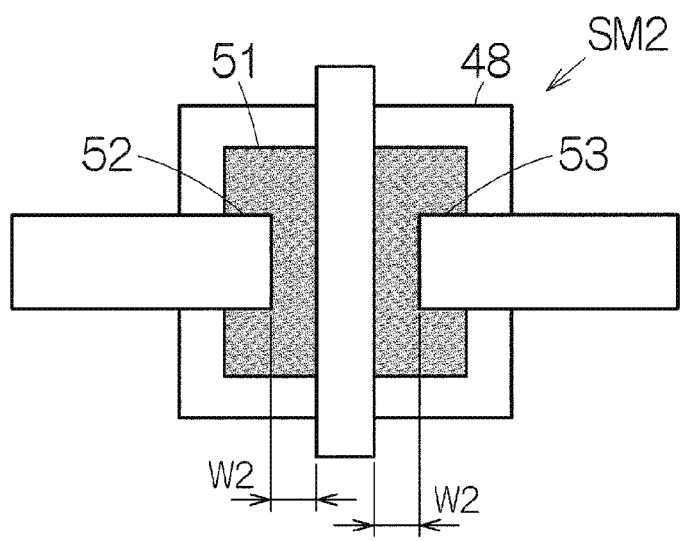
Figure 11C:
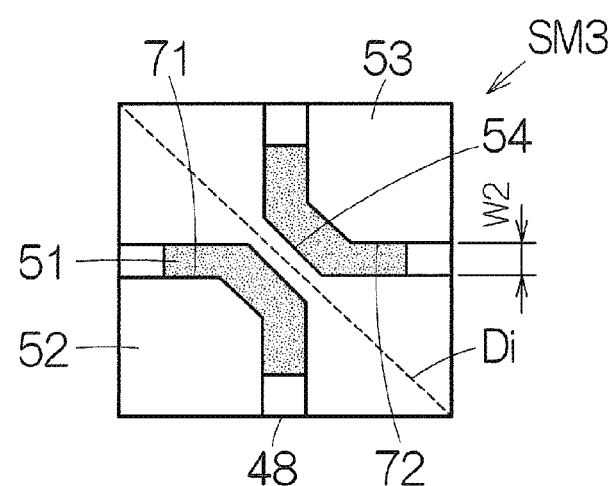

The present inventors examined the advantages of the second piezoelectric device 47. As shown in FIGS. 11A to 11C, in such an examination, a simulation model SM1 of a comparative example (FIG. 11A), a simulation model SM2 of the second piezoelectric device 47 (FIG. 11B), and a simulation model SM3 according to another embodiment (FIG. 11C) were constructed. In the simulation model SM1, the third electrode 54 was omitted from the second piezoelectric device 47. On the surface of the piezoelectric film 51, the end portion 53a of the second electrode 53 was made to face the end portion 53a of the first electrode 52. In the simulation model SM3, the third electrode 54 having a band shape was disposed along a diagonal line Di. The first electrode 52 was made to face the third electrode 54 over the entire length of a contour 71 on the piezoelectric film 51. Similarly, the second electrode 53 was made to face the third electrode 54 over the entire length of a contour 72 on the piezoelectric film 51. The distance W2 between electrodes was set to 5 [μm] for all electrodes. The receiving sensitivity and the electrostatic capacitance were calculated in the simulation models SM1, SM2, and SM3. The simulation models SM1, SM2, and SM3 are calculated based on the following dimensions. The length of the short side of the contour of the vibrating film was 40 μm, and the length of the short side of the piezoelectric film 51 was 32 μm. In addition, the vibrating film includes $SiO_2$ (1000 nm), $ZrO_2$ (400 nm), and PZT (1350 nm) in order from below. The thickness of each of the first, second, and third electrodes 52, 53, and 54 was 50 nm. As the piezoelectric tensor and the stiffness tensor of PZT used in the simulation, a data set of PZT-5H was adopted. In this case, the principal axis of the tensor was set to a direction perpendicular to the reference line BL (direction in which an initialization electric field was applied). The Young's moduli of $SiO_2$ and $ZrO_2$ were 75 GPa and 190 GPa, respectively. The Young's moduli of the first, second, and third electrodes 52, 53, and 54 were 200 GPa. Simulation was performed using a finite element method for realizing the piezoelectric effect.

The present inventors further constructed a simulation model in examining the advantages. As shown in FIGS. 12A to 12C, compared with the simulation models SM1, SM2, and SM3, the aspect ratio of each of the vibrating film 48 and the piezoelectric film 51 was changed in simulation models SM4, SM5, and SM6. The vibrating film 48 and the piezoelectric film 51 were formed in rectangular shapes, and the aspect ratio was set to 2. That is, the length of the long side was set to twice the length of the short side. The distance between electrodes was set to 5 [μm] for all electrodes. The receiving sensitivity and the electrostatic capacitance were similarly calculated in the simulation models SM4, SM5, and SM6.

Figure 13:
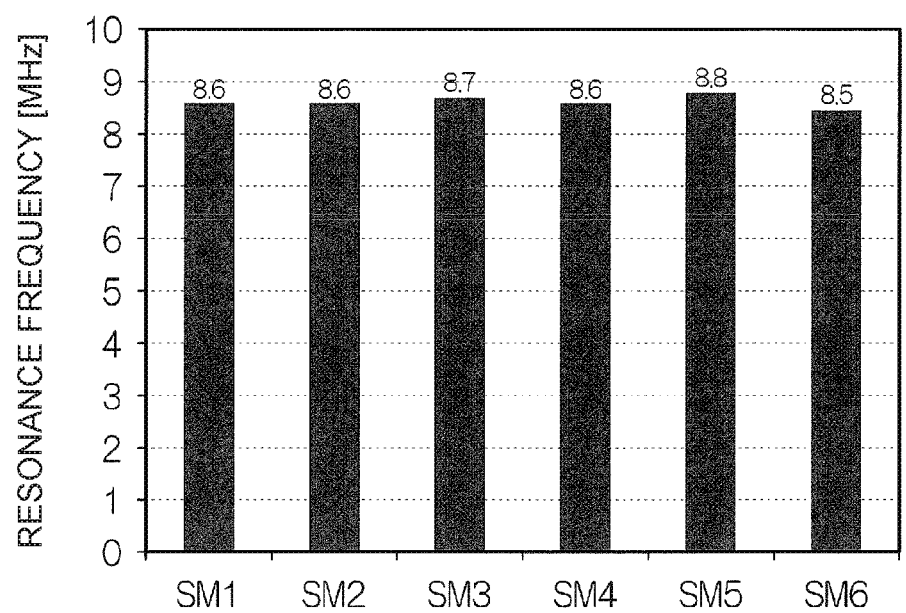
FIG. 13 is a graph showing a resonance frequency calculation result.
Figure 14A:
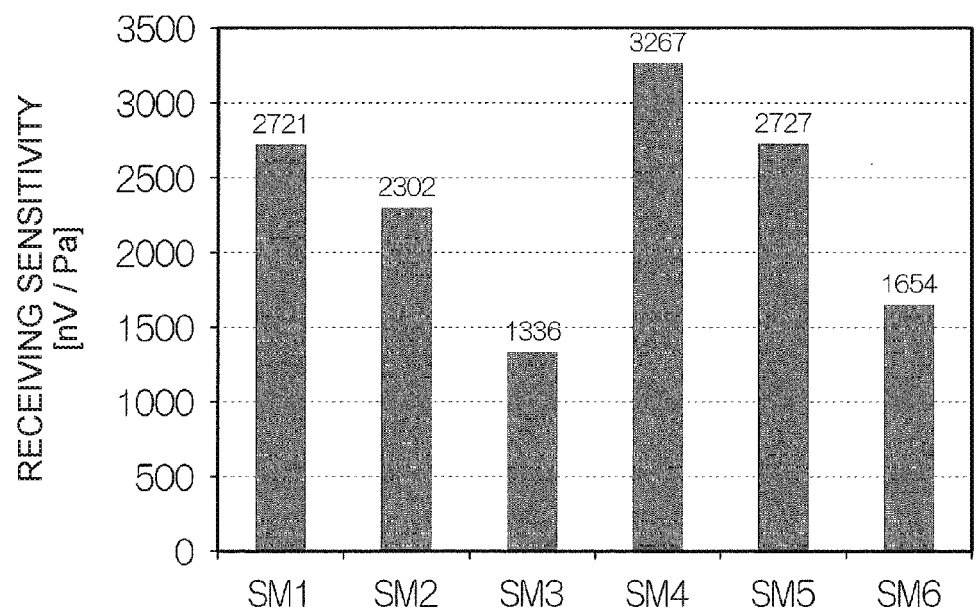
FIGS. 14A and 14B are graphs showing the receiving sensitivity and the electrostatic capacitance for each simulation model.

Although the resonance frequency of the vibrating film depends on other dimensions of the vibrating film, the resonance frequency of the simulation models SM1 to SM6 was changed in a range of 8.5 MHz to 8.8 MHz according to the setting of the dimensions as shown in FIG. 13. As shown in FIG. 14A, it was confirmed that the high receiving sensitivity was obtained in the simulation models SM1 and SM4. In the simulation model SM3 and SM6, it was observed that the receiving sensitivity was halved compared with the simulation models SM1 and SM4. On the other hand, in the simulation models SM2 and SM5, it was confirmed that the receiving sensitivity was reduced compared with the simulation models SM1 and SM4 but relatively high receiving sensitivity was secured. In addition, it was confirmed that the receiving sensitivity was improved in the simulation models SM4 to SM6 of the rectangular shape having an aspect ratio of 2 rather than the square simulation models SM1 to SM3.

This result shows that the amount of strain is always maximized in the short side direction and minimized in the long side direction. Although the first, second, and third electrodes 52, 53, and 54 are provided in parallel to the reference line BL, it is possible to obtain the maximum receiving sensitivity by setting the reference line BL in parallel to the long side direction. In other words, it is possible to obtain the maximum receiving sensitivity by providing the first, second, and third electrodes 52, 53, and 54 in parallel to the short side direction.

Next, simulation based on the finite element method in a case where the ratio between the short side and the long side in the rectangular shape of the vibrating film 48 was changed from 1:1 was performed. As an example, the short side and the long side of a vibrating film were set to 32.5 μm and 65 μm, respectively. One atmosphere was applied perpendicular to the vibrating film surface. The thickness of $SiO_2$ was set to 1000 nm, the thickness of $ZrO_2$ was set to 400 nm, the thickness of PZT was set to 1350 nm, and the thickness of an electrode was set to 50 nm. According to the simulation result, at the center of the vibrating film, a component of the strain in the short side direction was $-5.4 \times 10^{-5}$, and a component of the strain in the long side direction was $-7.0 \times 10^{-6}$. The strain in the short side direction is a value about 10 times larger in the absolute value than the strain in the long side direction. That is, in the vibrating film having a rectangular shape, it could be seen that the amount of strain was always maximized in the short side direction and minimized in the long side direction. Therefore, the first, second, and third electrodes 52, 53, and 54 are provided in parallel to the reference line BL, but it is possible to obtain the maximum receiving sensitivity by setting the reference line BL in parallel to the long side direction. In other words, it is possible to obtain the maximum receiving sensitivity by providing the first, second, and third electrodes 52, 53, and 54 in parallel to the short side direction.

Figure 14B:
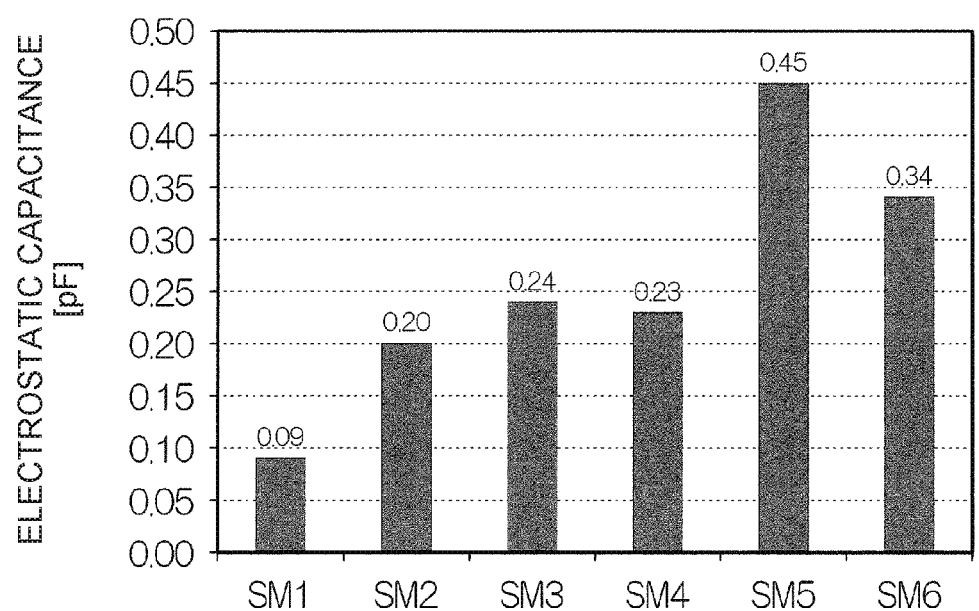

As shown in FIG. 14B, in the simulation models SM2 and SM5 having the third electrode, it was confirmed that the electrostatic capacitance per device was doubled compared with the simulation models SM1 and SM4 having no third electrode. This is because a plurality of electrode gaps are formed in a model having a third electrode so that the electrostatic capacitance is increased. In particular, in the rectangular simulation model SM5 having an aspect ratio of 2, a larger electrostatic capacitance than in the simulation model SM6 was obtained. As a result, it was found that, in the second piezoelectric device 47, a large electrostatic capacitance was obtained without degradation in the receiving sensitivity.

8. Structure of an Ultrasonic Device Unit According to Another Embodiment

Figure 15:
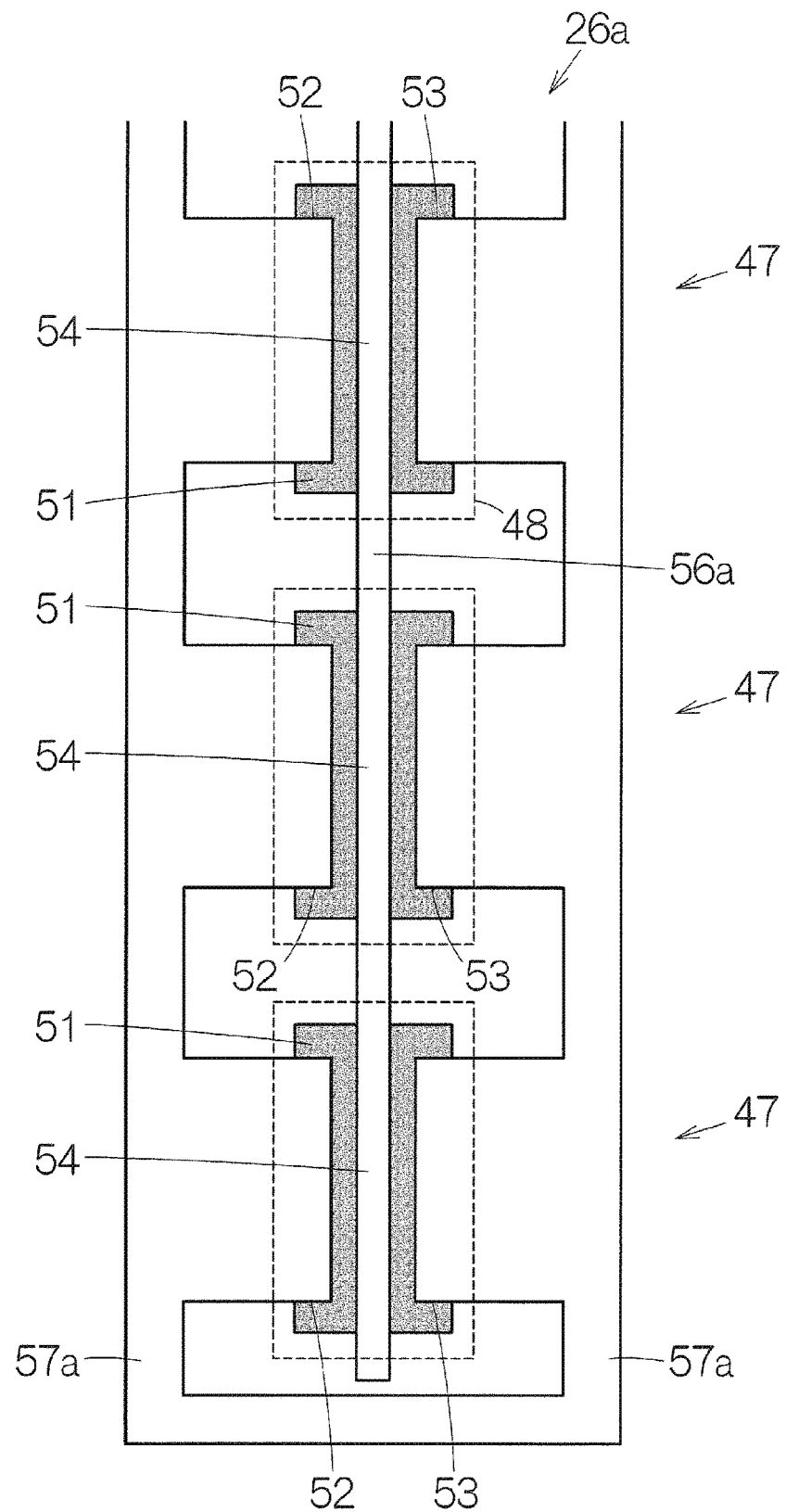
FIG. 15 is an enlarged partial plan view schematically showing the configuration of an ultrasonic device unit according to a second embodiment of the invention.

FIG. 15 schematically shows the structure of an ultrasonic device unit 26a according to a second embodiment of the invention. In the ultrasonic device unit 26a, second piezoelectric devices 47 are arranged in a slice direction in the receiving unit 35. A second signal electrode line (conductor) 56a forms a third electrode 54 in common with the plurality of second piezoelectric devices 47. The third electrode 54 traverses the surface of the corresponding piezoelectric film 51. A second common electrode line 57a forms a first electrode 52 in common with the plurality of second piezoelectric devices 47 arranged in the slice direction. Similarly, the second common electrode line 57a forms a second electrode 53 in common with the plurality of second piezoelectric devices 47 arranged in the slice direction. Other structures are the same as the ultrasonic device unit 26 of the first embodiment described above.

Figure 16:
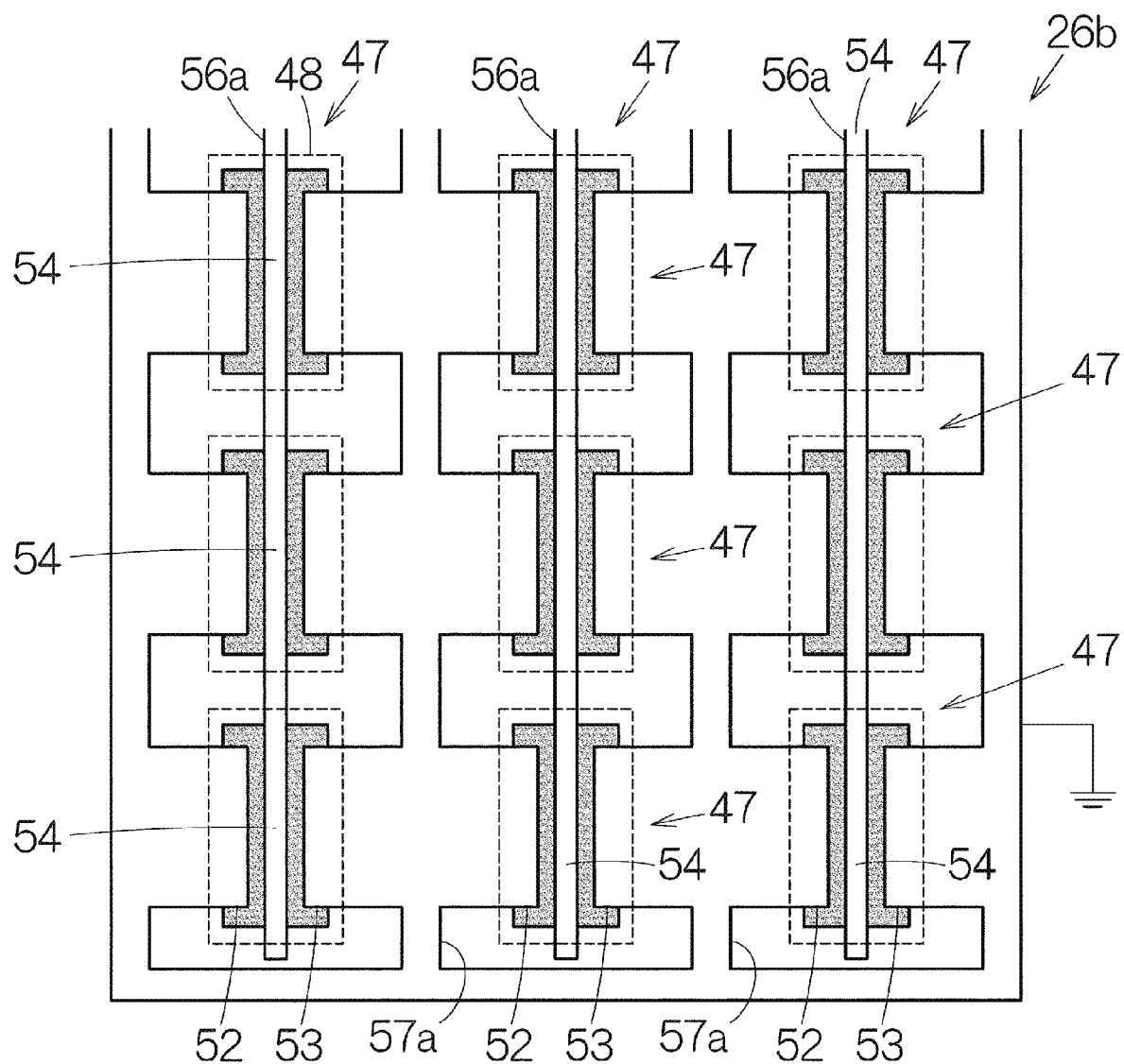
FIG. 16 is an enlarged partial plan view schematically showing the configuration of an ultrasonic device unit according to a third embodiment Of the invention.

FIG. 16 schematically shows the structure of an ultrasonic device unit 26b according to a third embodiment of the invention. In the ultrasonic device unit 26b, second piezoelectric devices 47 are arranged in a scanning direction and a slice direction in the receiving unit 35. A second signal electrode line (conductor) 56a forms a third electrode 54 in common with the plurality of second piezoelectric devices 47. The second signal electrode lines 56a extend in the slice direction in parallel to each other. The third electrode 54 traverses the surface of the corresponding piezoelectric film 51. A second common electrode line 57a forms first and second electrodes 52 and 53 in common with the plurality of second piezoelectric devices 47 arranged in the slice direction. A second common electrode line 57a forms first and second electrodes 52 and 53 in common with a pair of second piezoelectric devices 47 arranged in the scanning direction. The second common electrode lines 57a are connected to each other. Other structures are the same as the ultrasonic device units 26 and 26a of the first or second embodiment described above.

Figure 17:
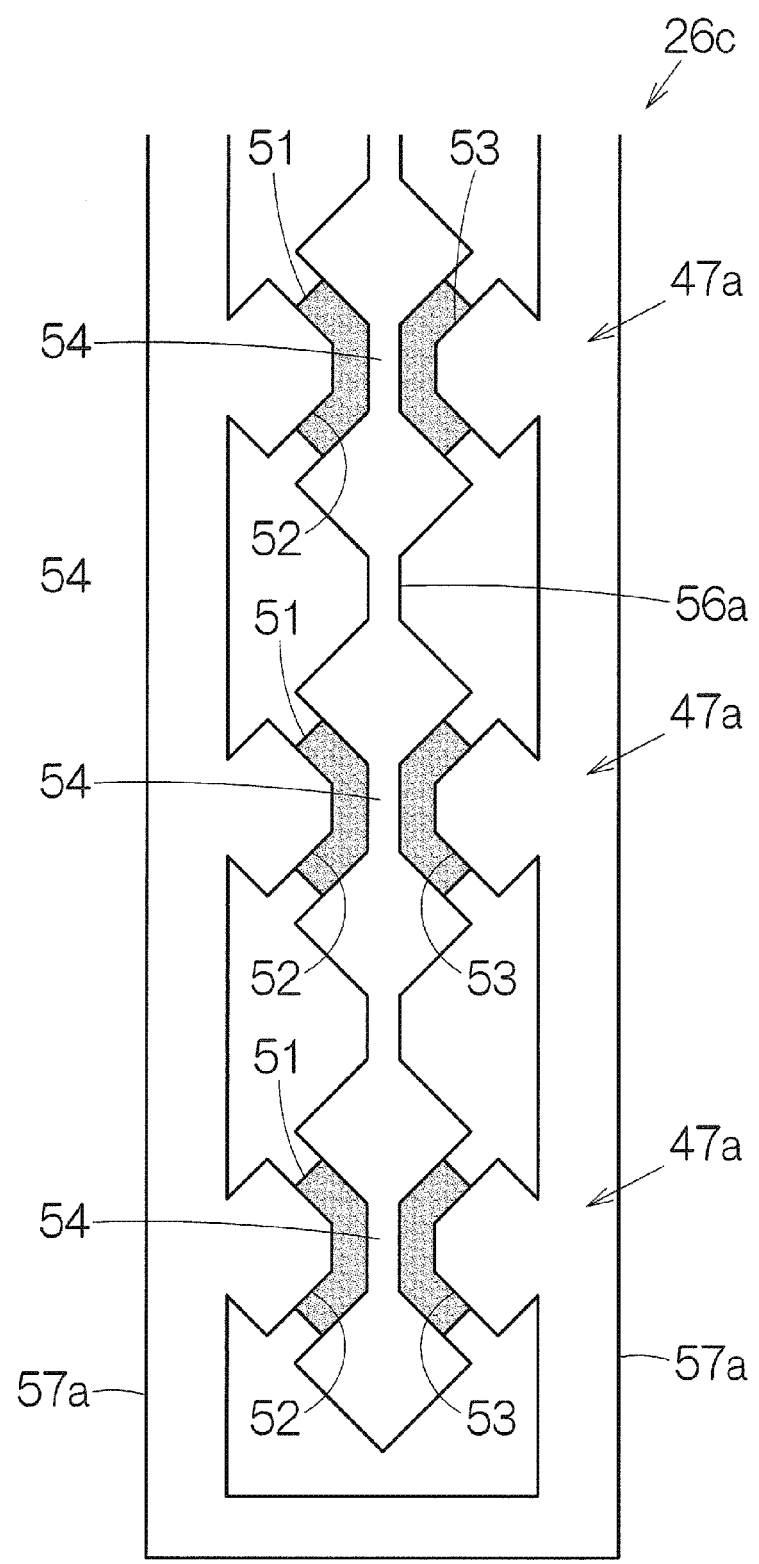
FIG. 17 is an enlarged partial plan view schematically showing the configuration of an ultrasonic device unit according to a fourth embodiment of the invention.

FIG. 17 schematically shows the structure of an ultrasonic device unit 26c according to a fourth embodiment of the invention. In the receiving unit 35 of the ultrasonic device unit 26c, the second piezoelectric device 47a is formed similar to the simulation model SM3 described above. The second piezoelectric devices 47a are arranged in a slice direction. A second signal electrode line (conductor) 56a forms a third electrode 54 in common with a plurality of second piezoelectric devices 47a. The third electrode 54 traverses the surface of the corresponding piezoelectric film 51. A second common electrode line 57a forms a first electrode 52 in common with the plurality of second piezoelectric devices 47a arranged in the slice direction. Similarly, the second common electrode line 57a forms a second electrode 53 in common with the plurality of second piezoelectric devices 47a arranged in the slice direction. Other structures are the same as the ultrasonic device unit 26 of the first embodiment described above.

While the embodiments have been described in detail above, as would be easily understood by those skilled in the art, various changes and modifications thereof can be made without departing from novel matters and effects of the invention. Accordingly, all of such modification examples are still included in the range of the invention. For example, in the specification or diagrams, a term which is described at least once together with different terms having a broader meaning or the same meaning can be replaced with the different terms in any parts of the specification or diagrams. In addition, the configurations and operations of the apparatus body 12, the ultrasonic probe 13, the element array 31, the ultrasonic transducer 32, and the like are not limited to those described in the present embodiment, and various modifications can be made.

The entire disclosure of Japanese Patent Application No. 2015-108929 filed on May 28, 2015 is expressly incorporated by reference herein.

What is claimed is:

1. A piezoelectric device, comprising:
 a vibrating film;
 a piezoelectric film that is provided on the vibrating film and has a first surface in contact with the vibrating film and a second surface on an opposite side to the first surface;
 first and second electrodes that are disposed at positions away from each other on the piezoelectric film and electrically connected to each other at a position which is not on the piezoelectric film; and
 a third electrode that is provided between the first and second electrodes and that is disposed at a position away from the first and second electrodes,
 wherein at least parts of contours of end portions of the first and second electrodes are defined in parallel to side portions of the third electrode.

2. The piezoelectric device according to claim 1,
 wherein, the first and second electrodes and the third electrode are positioned so as to form a voltage path of polarization processing along a direction of strain having a maximum value.

3. The piezoelectric device according to claim 1,
 wherein the third electrode is formed in a band shape passing through a center of the vibrating film in a plan view.

4. The piezoelectric device according to claim 3,
 wherein, in the piezoelectric film, strain occurs in an in-plane direction in a region including the center of the vibrating film.

5. The piezoelectric device according to claim 1,
 wherein the piezoelectric film is located on an inner side rather than along an edge shape of the vibrating film in a plan view.

6. The piezoelectric device according to claim 1,
 wherein a center of the piezoelectric film overlaps a center of the vibrating film.

7. The piezoelectric device according to claim 1,
 wherein the vibrating film has a rectangular shape in a plan view, and
 the first and second electrodes are separated from the third electrode in a direction along short sides of the vibrating film.

8. The piezoelectric device according to claim 7,
 wherein the piezoelectric device is formed symmetrically with respect to a reference line parallel to long sides of the vibrating film.

9. The piezoelectric device according to claim 8,
 wherein the third electrode has a first width in parallel to short sides of the piezoelectric film, and
 the first and second electrodes are separated from the third electrode in parallel to short sides of the piezoelectric film with a second width equal to or greater than the first width.

10. The piezoelectric device according to claim 1,
 wherein, between the first and third electrodes and between the second and third electrodes, a groove is formed on the second surface.

11. The piezoelectric device according to claim 1,
 wherein, between the first and second electrodes and the third electrode in a plan view, a material other than a conductor is disposed on the vibrating film.

* * * * *